(12) United States Patent
Akerele et al.

(10) Patent No.: US 12,672,708 B2
(45) Date of Patent: Jul. 7, 2026

(54) HAIR CLEANSING DEVICE FOR SEBUM REDUCTION AND REMOVAL

(71) Applicant: L'Oreal, Paris (FR)

(72) Inventors: Dominic Akerele, Brooklyn, NY (US); Maya Kelley, San Francisco, CA (US); Fred Orsita, Wayne, NJ (US)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 18/820,583

(22) Filed: Aug. 30, 2024

(65) Prior Publication Data

US 2026/0060400 A1    Mar. 5, 2026

(51) Int. Cl.
| | |
|---|---|
| *A61N 7/00* | (2006.01) |
| *A45D 19/02* | (2006.01) |
| *A61F 7/00* | (2006.01) |
| *A61N 5/06* | (2006.01) |
| *A45D 19/00* | (2006.01) |
| *A45D 44/00* | (2006.01) |

(52) U.S. Cl.
CPC ............... *A45D 19/02* (2013.01); *A61F 7/00* (2013.01); *A61N 5/0617* (2013.01); *A61N 7/00* (2013.01); *A45D 2019/0033* (2013.01); *A45D 2044/007* (2013.01); *A45D 2200/205* (2013.01); *A45D 2200/207* (2013.01); *A61F 2007/0008* (2013.01); *A61F 2007/0052* (2013.01); *A61F 2007/0087* (2013.01); *A61N 2005/0626* (2013.01); *A61N 2005/0644* (2013.01); *A61N 2005/0659* (2013.01); *A61N 2005/0661* (2013.01); *A61N 2005/0663* (2013.01); *A61N 2007/0034* (2013.01)

(58) Field of Classification Search
CPC .................. A61N 2007/0034; A61N 2007/034
See application file for complete search history.

(56) References Cited

U.S. PATENT DOCUMENTS

| | | |
|---|---|---|
| 9,687,508 B2 | 6/2017 | Anderson et al. |
| 10,172,644 B2 | 1/2019 | Ignon et al. |

(Continued)

FOREIGN PATENT DOCUMENTS

| | | | |
|---|---|---|---|
| JP | 2017029286 A | * | 2/2017 |
| WO | 2014210149 A1 | | 12/2014 |
| WO | WO-2023222781 A1 | * | 11/2023 ............... A61N 7/00 |

OTHER PUBLICATIONS

International Search Report and Written Opinion mailed Dec. 3, 2025 for corresponding PCT Application No. PCT/US2025/043306, filed Aug. 25, 2025; 15 pages.

*Primary Examiner* — Colin T. Sakamoto
(74) *Attorney, Agent, or Firm* — CHRISTENSEN O'CONNOR JOHNSON KINDNESS PLLC

(57) ABSTRACT

A device for reducing sebum, including a dispenser component configured to dispense a formula, a transducer component configured to apply an energy treatment, a vacuum component configured to apply suction, and a scraper component comprising one or more sebum extraction channels, where the scraper component is configured to contact a scalp of a user. Further, a method of reducing sebum with the device including dispensing the formula onto the scalp, applying the energy treatment to the scalp, moving the scraper across the scalp so that the sebum is directed into the one or more sebum extraction channels of the scraper, and suctioning the sebum into a sebum reservoir with the vacuum component.

14 Claims, 10 Drawing Sheets

(56)                    References Cited

U.S. PATENT DOCUMENTS

| | | | |
|---|---|---|---|
| 2006/0089632 A1* | 4/2006 | Barthe ................... | A61B 8/483 |
| | | | 606/27 |
| 2012/0059307 A1* | 3/2012 | Harris ...................... | A61P 1/04 |
| | | | 977/773 |
| 2012/0259252 A1* | 10/2012 | Thorn-Leeson ........ | A61P 17/00 |
| | | | 601/3 |
| 2013/0073001 A1* | 3/2013 | Campbell ............ | A61N 5/0616 |
| | | | 607/88 |
| 2015/0045723 A1 | 2/2015 | Paithankar et al. | |
| 2017/0080257 A1* | 3/2017 | Paunescu .......... | A61M 37/0092 |
| 2017/0165105 A1* | 6/2017 | Anderson ................ | A61F 7/02 |
| 2018/0344345 A1* | 12/2018 | Knowlton ............ | A61B 17/322 |
| 2020/0016342 A1 | 1/2020 | Ignon | |
| 2020/0367961 A1* | 11/2020 | Podmore .............. | A61N 5/0616 |
| 2021/0267344 A1 | 9/2021 | Besen et al. | |
| 2021/0267345 A1 | 9/2021 | Besen et al. | |
| 2022/0087406 A1 | 3/2022 | Kosecoff | |
| 2022/0088407 A1* | 3/2022 | Kosecoff .............. | A61N 5/0617 |
| 2023/0101556 A1 | 3/2023 | Akerele et al. | |
| 2024/0115025 A1 | 4/2024 | Charraud et al. | |
| 2025/0009104 A1* | 1/2025 | Wu ........................ | A45D 24/28 |

* cited by examiner

HAIR CLEANSING DEVICE FOR SEBUM REDUCTION AND REMOVAL

SUMMARY

In one aspect, disclosed herein is a device for removing sebum, including a dispenser component configured to dispense a formula, a transducer component configured to apply an energy treatment, a vacuum component configured to apply suction, and a scraper component comprising one or more sebum extraction channels, wherein the scraper component is configured to contact a scalp of a user.

In some embodiments, the device further includes a processor configured to direct the dispenser component, the transducer component, and the vacuum component, and communicatively couple the device to a smart device.

In some embodiments, the one or more sebum extraction channels comprise rectangular grooves. In some embodiments, the one or more sebum extraction channels are tapered. In some embodiments, the one or more sebum extraction channels comprise an array of vertical channels. In some embodiments, the one or more sebum extraction channels comprise triangular grooves. In some embodiments, the one or more sebum extraction channels are a first one or more sebum extraction channels disposed on a contact surface of the scraper component, and a second one or more sebum extraction channels are disposed on a second side of the scraper component, opposite the contact surface. In some embodiments, the one or more sebum extraction channels comprise one or more through holes on a contact edge of the scraper component.

In some embodiments, the energy treatment is ultrasonic vibration. In some embodiments, a frequency of the ultrasonic vibration is between about 20 kHz to about 50 kHz. In some embodiments, the energy treatment comprises light treatment. In some embodiments, the light treatment is selected from red light having a wavelength of about 620 nm to about 750 nm, ultraviolet (UV) light having a wavelength of about 100 nm to about 400 nm, and infrared (IR) light having a wavelength of about 780 nm to about 1 mm. In some embodiments, the energy treatment comprises heat treatment. In some embodiments, the heat treatment heats the scalp to about 28 degrees Celsius to about 30 degrees Celsius.

In another aspect, disclosed herein is a method of reducing sebum with the device described herein. In some embodiments, the method includes dispensing the formula onto the scalp, applying the energy treatment to the scalp, moving the scraper component across the scalp so that the sebum is directed into the one or more sebum extraction channels of the scraper component, and suctioning the sebum into a sebum reservoir with the vacuum component.

In some embodiments, the device does not contact the scalp when the formula is dispensed.

In some embodiments, the method further includes diagnosing a condition of the scalp with a smart device. In some embodiments, the method further includes tracking the condition over time, and modulating therapy based on the tracked condition. In some embodiments, the method further includes modulating therapy based on the diagnosed condition. In some embodiments, modulating the therapy includes identifying one or more areas of the scalp for therapy, modulating an ingredient of the formula, adjusting a temperature of the energy treatment, adjusting a frequency of the energy treatment, adjusting a wavelength of the energy treatment, or a combination thereof.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Figure 1:
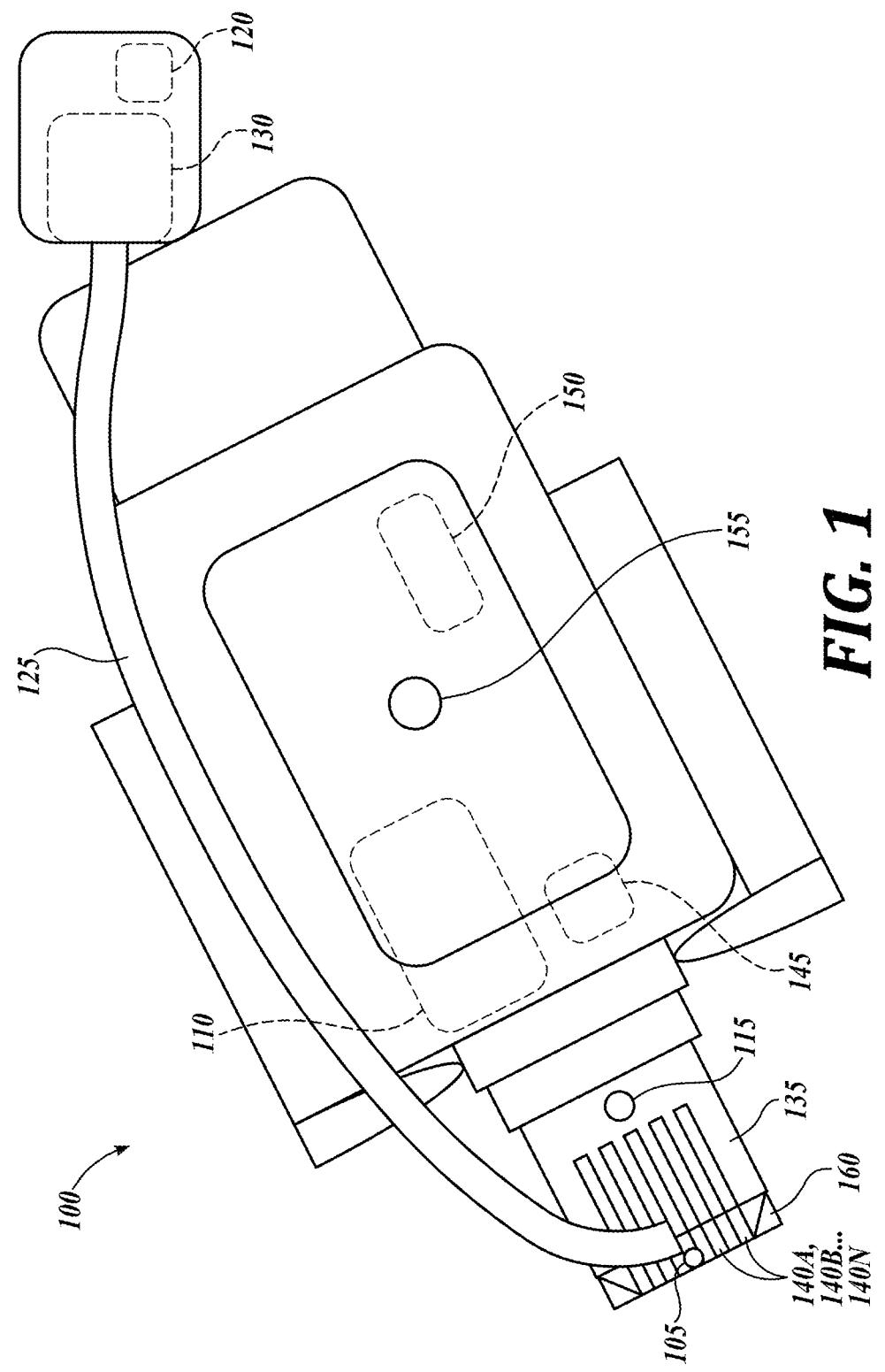
FIG. 1 is an example device for removing sebum, in accordance with the present technology.

The foregoing aspects and many of the attendant advantages of this invention will become more readily appreciated as the same become better understood by reference to the following detailed description, when taken in conjunction with the accompanying drawings.

DETAILED DESCRIPTION

Disclosed herein are devices, systems, and methods for removing, scraping, wicking, collecting, absorbing, cleaning, vacuuming etc., sebum from the scalp. While the term "sebum" is used throughout, it should also be understood that the devices, systems, and methods disclosed herein may remove any number of substances from the scalp, such as residual cosmetics products, dirt, sweat, dead skin, and bacteria. In some embodiments, the devices, systems, and methods disclosed herein allow a user to clean their scalp and remove sebum without utilizing much or any water. In some embodiments, the device includes a dispenser component configured to apply a formula configured to clean the scalp, maintain a hair style, such as curls or waves, replenish hair style, deliver fragrance, prevent acne, or combinations thereof. In some embodiments, the device includes a dispenser component configured to apply a formula configured to prevent or reduce irritation, redness, dryness, flakiness, and the like. In some embodiments, the device includes treatment components configured to apply an energy treatment. Examples of energy treatments include ultrasonic vibration, light treatment, and/or heat treatment. Examples of energy treatment components include acoustic transducer components, ultrasonic transducer components, electromagnetic energy transduces, thermal energy transduces, electromechanical transduces, and the like, or combinations thereof.

In some embodiments, the energy treatment is configured to melt, loosen and/or liquify sebum from the scalp. The energy treatment may also emulsify the formula. In some embodiments, the device also includes a vacuum component configured to apply suction to the scalp, hair, skin, or other biological surfaces. The vacuum component may remove the loosened or liquified sebum from the scalp, such as with a suction tube, into a sebum reservoir. The sebum reservoir may be external to or internal to the device. In some embodiments, the sebum reservoir is removable from the device for cleaning or replacement. In some embodiments, the device further includes a scraper component having one or more sebum extraction channels. The sebum extraction channels may collect sebum from the scalp as the scraper component is moved across the scalp. In some embodiments, the one or more sebum extraction channels are configured to direct the sebum to the vacuum component, to remove the sebum from the scalp. A variety of shapes of sebum extraction channels may be used, as described herein.

In some embodiments, the devices, systems, and methods disclosed herein include components configure to deliver a mechanical stimulus having a frequency and for a duration sufficient to accelerate the transformation of a high viscosity semi-solid or solid non-Newtonian composition like sebum to a less viscous composition more suitable for removal via vacuum, aspiration, capillary action, or the like.

In some embodiments, the device may be communicatively coupled to a smart device. In some embodiments, the smart device includes an application configured to direct the device, diagnose a condition of the scalp, track the efficacy of the device over time, and/or recommend or modulate therapy delivered by the device, including the formula, the energy treatment, and/or the suctioning. In some embodiments, some or all of these functions may be carried out with an artificial intelligence (AI) algorithm, such as a Large Language Model (LLM).

Further described herein are methods for using the devices and systems disclosed herein. In some embodiments, therapy can be delivered by the device simultaneously or sequentially.

FIG. 1 is an example device 100 for removing sebum, in accordance with the present technology. In some embodiments, the device 100 includes a dispenser component 105, a transducer component 115, a vacuum component 120, and a scraper component 135 having one or more sebum extraction channels 140A, 140B . . . 140N.

Figure 2:
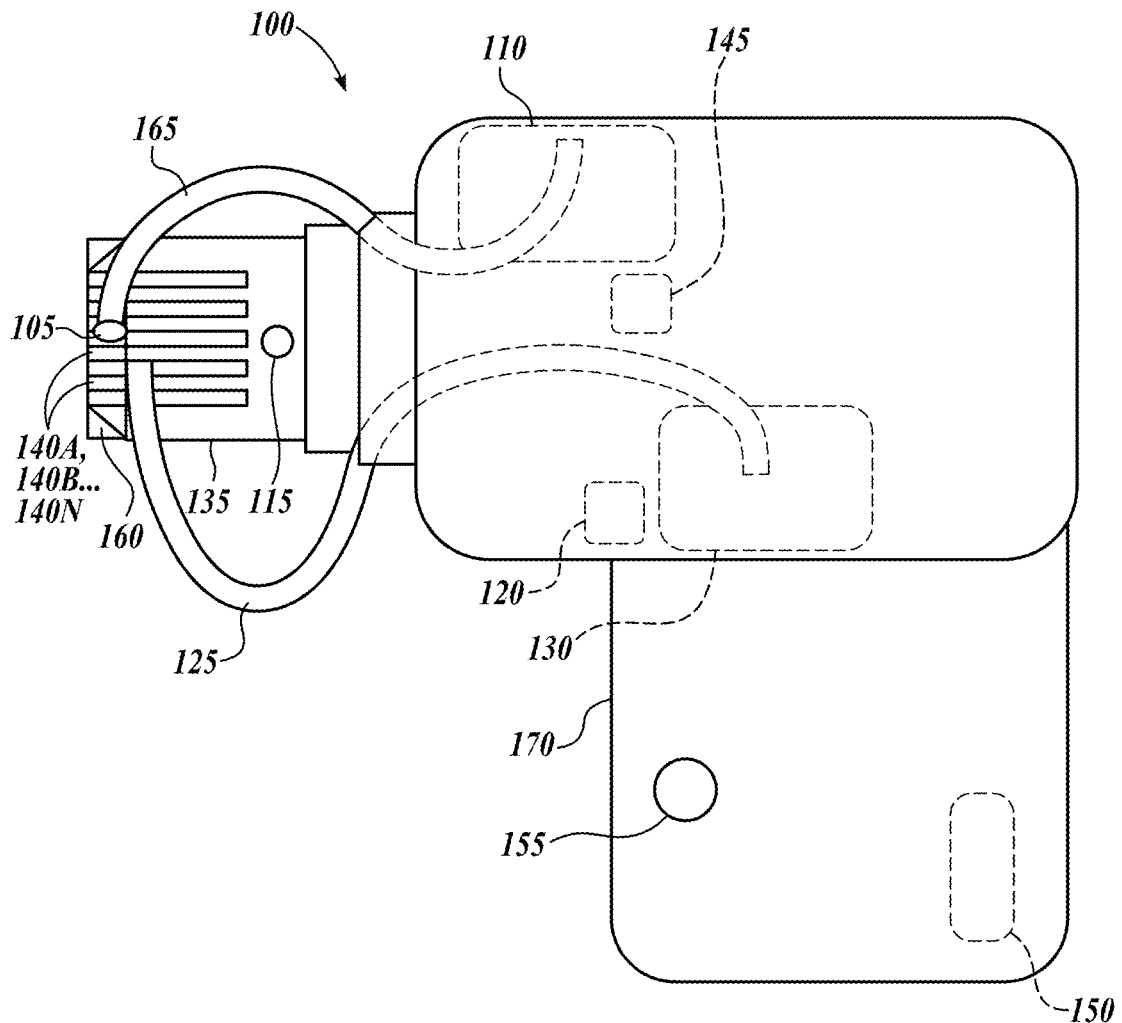
FIG. 2 is another example device for removing sebum, in accordance with the present technology.

In some embodiments, the dispenser component 105 is configured to dispense one or more formulas onto a user's scalp. In some embodiments, the dispenser component 105 is located on or below the scraper component 135. In some embodiments, the dispenser component 105 is a nozzle, pump, or sprayer. In some embodiments, the dispenser component is configured to dispense the formula as droplets, mist, or the like. In some embodiments, the dispenser component can apply formula to the scalp without touching the scalp. In some embodiments, the dispenser component is fluidly coupled to a formula reservoir 110. The formula reservoir may contain the one or more formulas. In some embodiments, the formula reservoir 110 may be fluidly coupled with a formula tube (such as shown in FIG. 2). It should be understood that components shown with dashed lines are internal to device 100. While the formula reservoir 110 is shown inside the device 100, it should be understood that the formula reservoir 110 may also be external to the device. In some embodiments, the formula reservoir 110 is configured to receive a container of formula, such as a pod or packet. In some embodiments, the formula reservoir 110 may pierce or open the formula container. In some embodiments, the container of formula may be configured to dissolve within the formula reservoir 110. In some embodiments, a plurality of formula reservoirs may be included in or external to the device 100. In some embodiments, each formula reservoir 110 of the plurality of formula reservoirs may each contain a different formula or active ingredient. In such embodiments, the composition of or amount of formulas may be modulated.

In some embodiments, the one or more formulas are configured for cleaning the scalp. In some embodiments, the one or more formulas are configured to clean the scalp without the use of water. In some embodiments, the one or more formulas are configured for adding softness to hair, smoothness to hair, or a combination thereof. In some embodiments, the one or more formulas are configured to maintain a style of hair, such as curls or waves. In some embodiments, the one or more formulas are configured to kill bacteria, reduce redness of the scalp, reduce or prevent dandruff, or a combination thereof. In some embodiments, the one or more formulas are configured to balance or rebalance a microbiome of the scalp. In some embodiments, the one or more formulas include disodium cocoyl glutamate, coco-betaine, decyl glucoside, rhamnolipids, behentrimonium chloride, cetrimonium chloride, brassicamidopropyl dimethylamine, ferulic acid, neurophroline, niacinamide, melatonin, proxylane, hyaluronic acid (HA), or a combination thereof. In some embodiments, the one or more formulas are alcohol free. In some embodiments, the one or more formulas are free from surfactants.

In some embodiments, the device 100 includes a transducer component 115. In some embodiments, the transducer component 115 is configured to apply an energy treatment to the scalp. Multiple types of energy therapy may be applied, either alone or in combination. While referred to as a transducer component 115, it should be understood that the transducer component 115 may take many forms, including a heater, a light-emitting diode (LED), a vibrator, or the like. Similarly, the energy treatment may take any number of forms.

As an example, in some embodiments, the energy treatment is ultrasonic vibration. The ultrasonic vibration (or ultrasonic energy) may loosen sebum from the scalp and/or emulsify the one or more formulas applied to the scalp. In some embodiments, the ultrasonic vibration may regulate sebaceous glands and remove accumulated sebum. In some embodiments, the ultrasonic vibration saponifies sebum on the scalp, making it easier to remove. In some embodiments, a frequency of the ultrasonic vibration is between about 20 kHz to about 50 kHz.

In another example, the energy treatment comprises light treatment. In such embodiments, the transducer component 115 may be one or more LEDs. In some embodiments, the light treatment penetrates deep into the skin and affects sebum production while also reducing inflammation and irritation of the scalp. In some embodiments, the light treatment can be used to treat acne by reducing sebum production and the size of sebaceous glands. In some embodiments, the light treatment is selected from red light having a wavelength of about 620 nm to about 750 nm, ultraviolet (UV) light having a wavelength of about 100 nm to about 400 nm, and infrared (IR) light having a wavelength of about 780 nm to about 1 mm.

In yet another example, the energy treatment comprises heat treatment. In some embodiments, heat treatment includes heating, cooling, or a combination thereof. In some embodiments, the heat treatment is configured to heat sebum on the scalp so that the sebum moves from a solid state to a liquid state. In some embodiments, the heat treatment heats the scalp to about 28 degrees Celsius to about 30 degrees Celsius.

While three examples of energy treatment have been described, it should be understood that in some embodiments, a combination of some or even all of the described energy treatments may be utilized by a single device 100. For example, the device 100 may be configured to apply energy treatment in the form of both ultrasonic vibration and heat treatment.

In some embodiments, the device 100 further includes a vacuum component 120 configured to apply suction to the scalp. In some embodiments, the vacuum component pulls sebum from the scalp and into a sebum reservoir 130 with a suction tube 125. In some embodiments, the sebum reservoir 130 is external to the device 100, but it should be understood that in other embodiments, the sebum reservoir 130 is internal to the device 100 (as shown in FIG. 2). In some embodiments, the vacuum component 120 pulls sebum from the one or more sebum extraction channels 140A, 140B . . . 140N. In some embodiments, the vacuum component 120 is able to pull sebum from the scalp because the energy treatment has loosened and/or liquified sebum on the scalp.

In some embodiments, the device 100 has a scraper component 135 configured to remove sebum from the scalp with one or more sebum extraction channels 140A, 140B . . . 140N. In some embodiments, the one or more sebum extraction channels 140A, 140B . . . 140N are configured to move sebum from the scalp to the suction tube 125 for removal. In some embodiments, the one or more sebum extraction channels 140A, 140B . . . 140N utilize capillary action to remove sebum. The scraper component is shown and described in further detail in FIGS. 3A-8B.

In some embodiments, the device 100 further comprises a processor 145, a battery 150, an actuator 155, and a guard 160.

Figure 9:
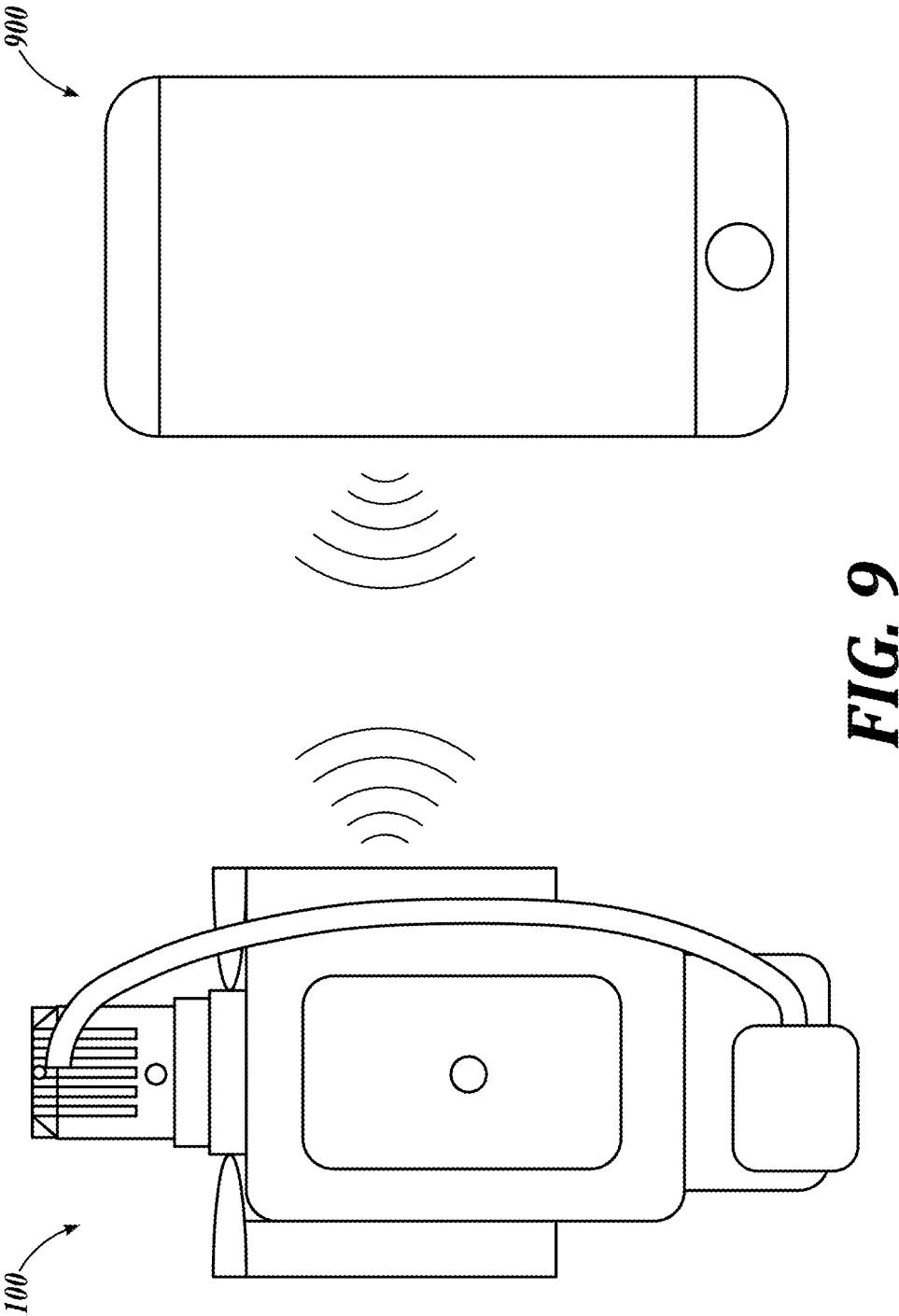
FIG. 9 is an example system for removing sebum, in accordance with the present technology.

In some embodiments, the processor 145 is configured to direct the dispenser component, the transducer component, and/or the vacuum component, and communicatively couple the device to a smart device. In some embodiments, the processor may control the device 100 in response to a user actuating the actuator 155. In some embodiments, the processor 145 may communicatively couple the device 100 to a smart device, as shown in FIG. 9. In some embodiments, a user may press a button, tap a screen, or otherwise control the processor 145 from an application on the smart device. In some embodiments, the actuator 145 is a button, switch, toggle, or the like. In some embodiments, the actuator 145 is a capacitance-type touch button. In some embodiments, the device further includes a battery 150. In some embodiments, the battery 150 may be a single use or rechargeable battery. In some embodiments, the battery 150 may be an inductive element configured to facilitate wireless charging. In some embodiments, the battery 150 may couple with a wire (not shown) for wired charging of the device 100.

In some embodiments, the guard 160 may be used to protect the one or more sebum extraction channels 140A, 140B . . . 140N from dust or other contaminants. In some embodiments, the guard 160 directs collected sebum to the suction tube 125. In some embodiments, the guard 160 is transparent, as shown in FIG. 1. In other embodiments, the guard 160 is opaque.

In operation, the device 100 is configured to apply formula to the scalp with the dispenser component 105, apply an energy treatment to the scalp to loosen or liquify sebum with the transducer component 115, remove sebum from the scalp with the one or more sebum extraction channels 140A, 140B . . . 140N, and suction sebum away from the scalp with a vacuum component 120. In some embodiments, the device 100 may further be configured to provide vibration, oscillation, or other tactile treatment to the scalp. As disclosed herein, the term "therapy" may be used to describe the application of the one or more formulas, the energy treatment, the suction, and/or tactile treatment. In some embodiments, the therapy may be delivered contemporaneously or simultaneously, that is, the one or more formulas may be dispensed contemporaneously with the energy treatment and the suction. In some embodiments, the therapy may be delivered sequentially, that is, the one or more formulas may be dispensed first, the energy therapy may be applied second, and the suction may be applied third. One skilled in the art should understand that the therapy may be delivered sequentially in a different order.

FIG. 2 is another example device 100 for removing sebum, in accordance with the present technology. In some embodiments, the device 100 includes a dispenser component 105, a formula reservoir 110, a transducer component 115, a vacuum component 120, a suction tube 125, a sebum reservoir 130, a scraper component 135 having one or more sebum extraction channels 140A, 140B . . . 140N, a processor 145, a battery 150, an actuator 155, and/or a guard 160 as described herein. In some embodiments, the device 100 further includes a formula tube 165 and a handle 170.

In some embodiments, the example device 100 has a handle 170 configured to make the device 100 handheld. In some embodiments, the actuator 155 is located on the handle to allow the user to actuate the actuator 155 while holding the handle 170. In some embodiments, one or more components of the device 100 may be included in the handle 170 of the device. For example, as shown in FIG. 2, the battery 150 is internal to the handle 170. It should be understood that other components, such as the formula reservoir 110, the sebum reservoir 130, the processor 145, or the vacuum component 120 may be included internally inside the handle 170. It should also be understood that components having dashed lines are internal to the device 100 and/or the handle 170.

In some embodiments, the formula reservoir 110 may be fluidly coupled with the formula tube 165. In some embodiments, the formula tube 165 spans from the scraper component 135 to the formula reservoir 110, and internal to the device 100. In some embodiments, the dispenser component 105 is located at an end of the formula tube 165, as shown in FIG. 2. In some embodiments, the dispenser component 105 is simply the opening of the formula tube 165. In other embodiments, the dispenser component 105 is a pump, sprayer, nozzle, or the like, as described herein.

The scraper component 135 of the device 100 may include one or more sebum extraction channels 140A, 140B, 140C . . . 140N configured to direct sebum to the sebum reservoir 130. As shown in FIGS. 3A-8B, in some embodiments, the scraper component 135 includes a contact surface CS and a contact edge CE. In some embodiments, a second side opposite the contact surface CS contacts the scalp of a user, and sebum contacts the contact surface CS. As the second side opposite the contact surface CS moves across the scalp, sebum is collected in the one or more sebum extraction channels 140A, 140B, 140C . . . 140N. In some embodiments, the scraper component 135 further includes a contact edge CE. In some embodiments, such as shown in FIGS. 3A-3B and 5A-8B, sebum enters the one or more sebum extraction channels 140A, 140B, 140C . . . 140N of the scraper component 135.

Figure 3B:
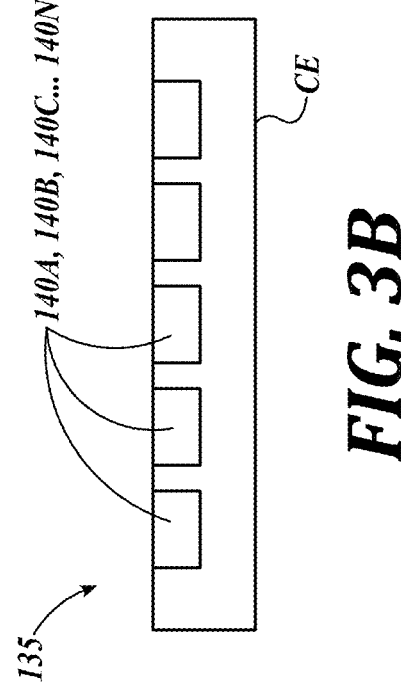
FIGS. 3A-3B are example top-down and front views, respectively, of an example scraper component, in accordance with the present technology.
Figure 3A:
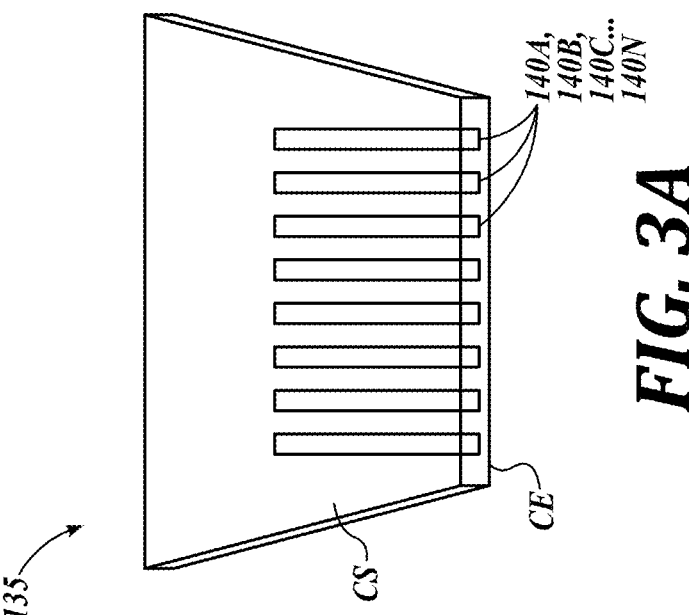

FIGS. 3A-3B are example top-down and front views, respectively, of an example scraper component 135, in accordance with the present technology. In some embodiments, the one or more sebum extraction channels 140A, 140B, 140C . . . 140N are rectangular grooves. In some embodiments, the rectangular grooves are recessed into the contact surface CS of the scraper component 135. Sebum may be channeled through the contact edge CE and into the rectangular grooves. Then, the sebum may be suctioned up or otherwise removed, such as with the vacuum component (as shown in FIGS. 1-2).

Figure 4B:
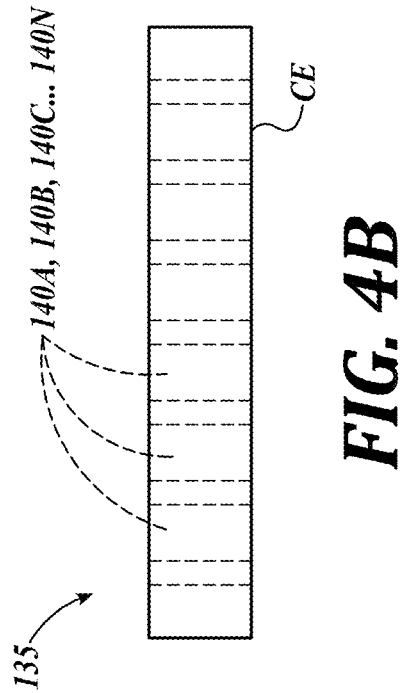
FIGS. 4A-4B are example top-down and front views, respectively, of another example scraper component, in accordance with the present technology.
Figure 4A:
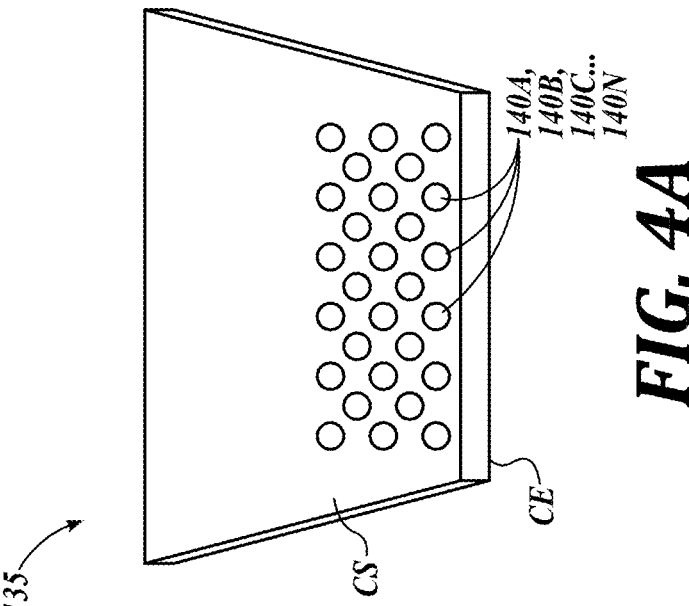
Figure 6B:
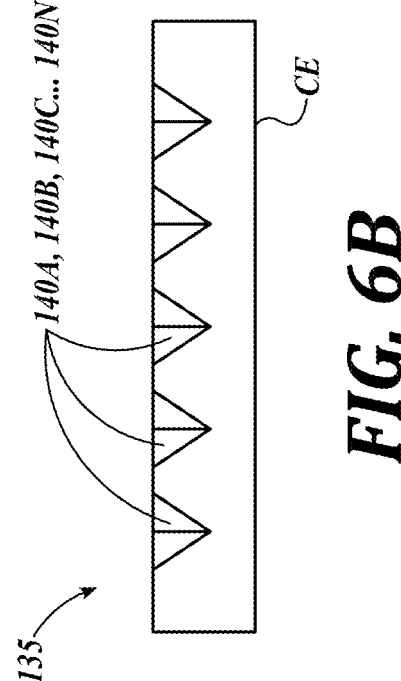
FIGS. 6A-6B are example top-down and front views, respectively, of another example scraper component, in accordance with the present technology.

FIGS. 4A-4B are example top-down and front views, respectively, of another example scraper component 135, in accordance with the present technology. In some embodiments, the one or more sebum extraction channels 140A, 140B, 140C . . . 140N are an array of vertical channels. In some embodiments, the vertical channels collect sebum like a foil shaver. When the vertical channels are used, there may not be an opening on the contact edge CE. FIG. 6B shown the contact edge of the scraper component 135 of FIG. 6A. The vertical channels through the contact surface CS are shown as dashed lines, to indicate they are internal to the scraper component 135.

Figure 5B:
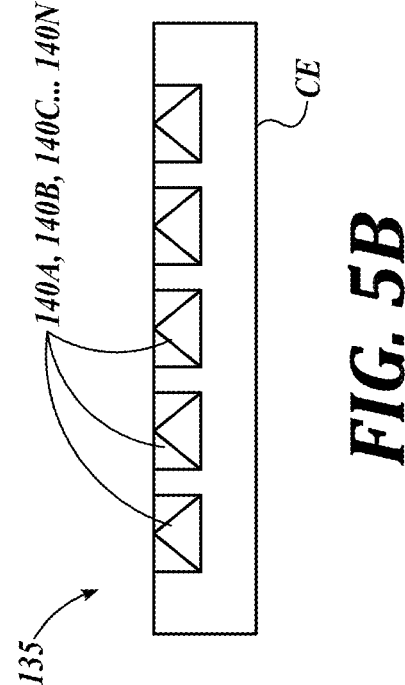
FIGS. 5A-5B are example top-down and front views, respectively, of yet another example scraper component, in accordance with the present technology.
Figure 5A:
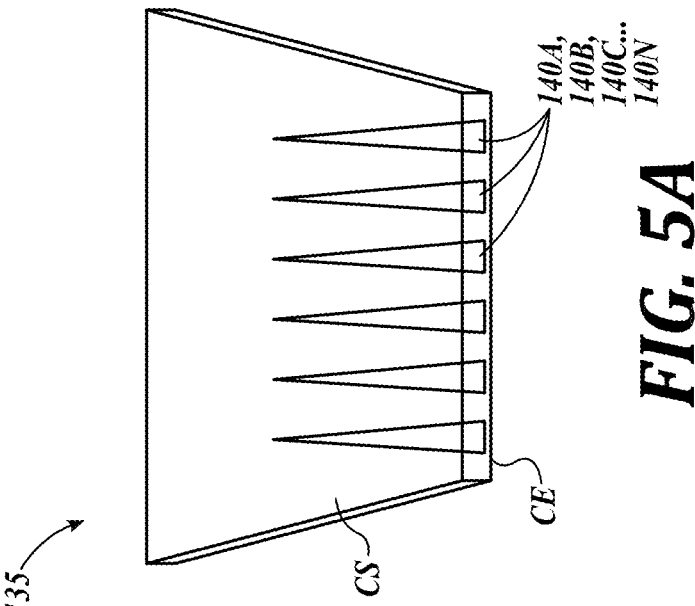

FIGS. 5A-5B are example top-down and front views, respectively, of yet another example scraper component 135, in accordance with the present technology. In some embodiments, the one or more sebum extraction channels 140A, 140B, 140C . . . 140N are tapered. In some embodiments, the one or more sebum extraction channels 140A, 140B, 140C . . . 140N may be rectangular at the contact edge CE and then taper to a substantially triangular shape across the contact surface CS. In some embodiments, by tapering the one or more sebum extraction channels 140A, 140B, 140C . . . 140N, the capillary rise may be increased. In this way, the tapered one or more sebum extraction channels 140A, 140B, 140C . . . 140N may further encourage sebum to move through the one or more sebum extraction channels 140A, 140B, 140C . . . 140N.

Figure 6A:
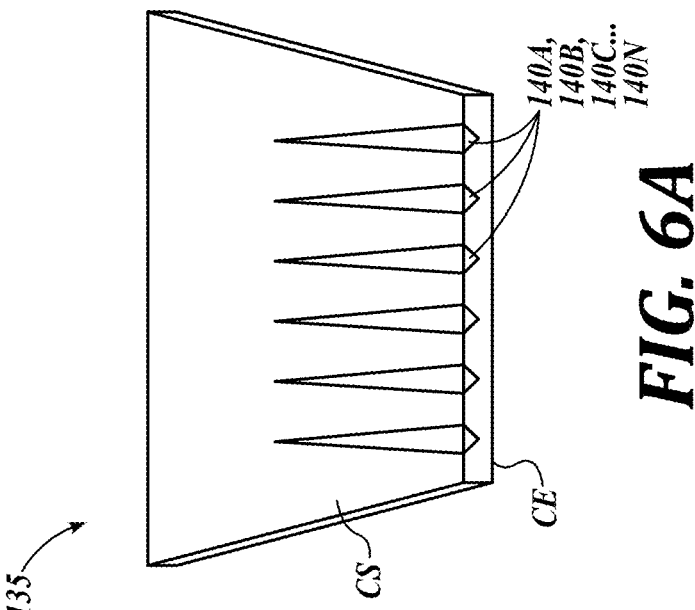

FIGS. 6A-6B are example top-down and front views, respectively, of another example scraper component 135, in accordance with the present technology. In some embodiments, the one or more sebum extraction channels 140A, 140B, 140C . . . 140N comprise triangular grooves. In some embodiments, capillary height may be increased when the one or more sebum extraction channels 140A, 140B, 140C . . . 140N have triangular cross-sections, as shown in FIG. 6B.

Figure 7B:
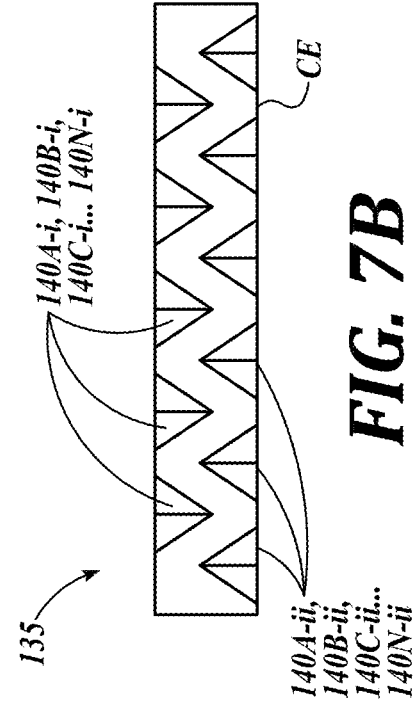
FIGS. 7A-7B are example top-down and front views, respectively, of another example scraper component, in accordance with the present technology.
Figure 7A:
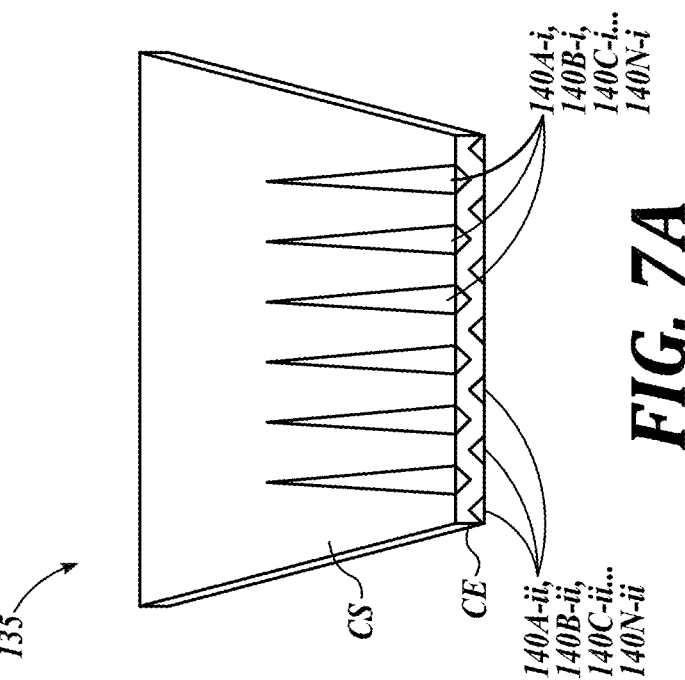

FIGS. 7A-7B are example top-down and front views, respectively, of another example scraper component 135, in accordance with the present technology. In some embodiments, the one or more sebum extraction channels are a first one or more sebum extraction channels 140A-i, 140B-i, 140C-i . . . 140N-i disposed on the contact surface CS of the scraper component 135, and a second one or more sebum extraction channels 140A-ii, 140B-ii, 140C-ii . . . 140N-ii are disposed on a second side of the scraper component, opposite the contact surface. In such embodiments, the two-sided scraper component 135 double the space efficiency of the scraper component 135. Accordingly, in some embodiments, the scraper component 135 having the first one or more sebum extraction channels 140A-i, 140B-i, 140C-i . . . 140N-I and the second one or more sebum extraction channels 140A-ii, 140B-ii, 140C-ii . . . 140N-ii may remove more sebum from the scalp.

Figure 8B:
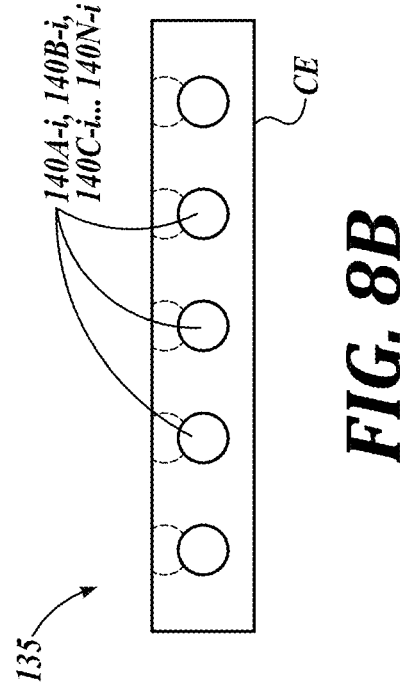
FIGS. 8A-8B are example top-down and front views, respectively, of yet another example scraper component, in accordance with the present technology.
Figure 8A:
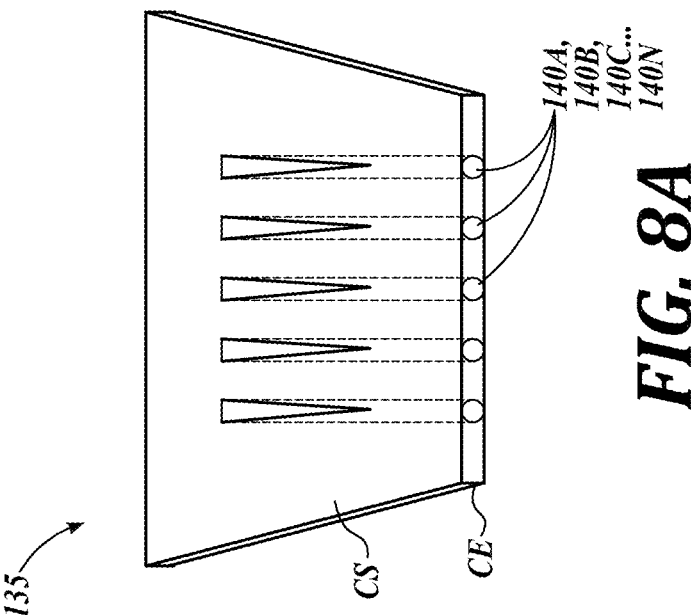

FIGS. 8A-8B are example top-down and front views, respectively, of yet another example scraper component 135, in accordance with the present technology. In some embodiments, the one or more sebum extraction channels 140A, 140B, 140C . . . 140N comprise one or more through holes on the contact edge CE of the scraper component 135. In such embodiments, the holes in the contact edge CE direct sebum into the through holes of the scraper component 135. By enclosing the one or more sebum extraction channels 140A, 140B, 140C . . . 140N, capillary action may be increased.

It should be understood that the scraper components 135 shown in FIGS. 3A-8B may all be utilized with a guard such as shown in FIGS. 1-2. In some embodiments, the guard may further work with the one or more sebum extraction channels 140A, 140B, 140C . . . 140N to direct sebum into a sebum reservoir.

FIG. 9 is an example system for removing sebum, in accordance with the present technology. In one aspect, disclosed herein is a system for removing sebum including a device 100, as described in detail herein, and a smart device 900. In some embodiments, the device 100 and the smart device 900 are communicatively coupled. In some embodiments, the device 100 and the smart device 900 may be communicatively coupled with Wi-Fi, a wireless connection such as Bluetooth® Low Energy (BLE), Zigbee, or the like. In some embodiments, the device 100 and the smart device 900 may be communicatively coupled with a wired connection.

In some embodiments, the smart device 900 may include an application configured to control the device 100, track the efficacy of the device 100, and/or modulate the therapy of the device 100. In some embodiments, the application may utilize artificial intelligence (AI) not limited to a generative AI algorithm, an AI algorithm utilizing supervised or unsupervised learning, a machine learning (ML) algorithm, a large language model (LLM), or the like. In some embodiments, AI may be utilized to diagnose a condition of the scalp, such as excess sebum, dirtiness, dandruff, irritation, or like. In some embodiments, AI may be utilized to track progress with the condition over time. In some embodiments, AI may be utilized to recommend or modulate therapy of the device 100, including identifying one or more areas of the scalp for therapy, modulating an ingredient of the formula, adjusting a temperature of the energy treatment, adjusting a frequency of the energy treatment; adjusting a wavelength of the energy treatment, or a combination thereof. In some embodiments, AI may be further utilized to determine a severity of the condition. One skilled in the art should recognize that these functions may also be carried out without the use of AI.

Figure 10:
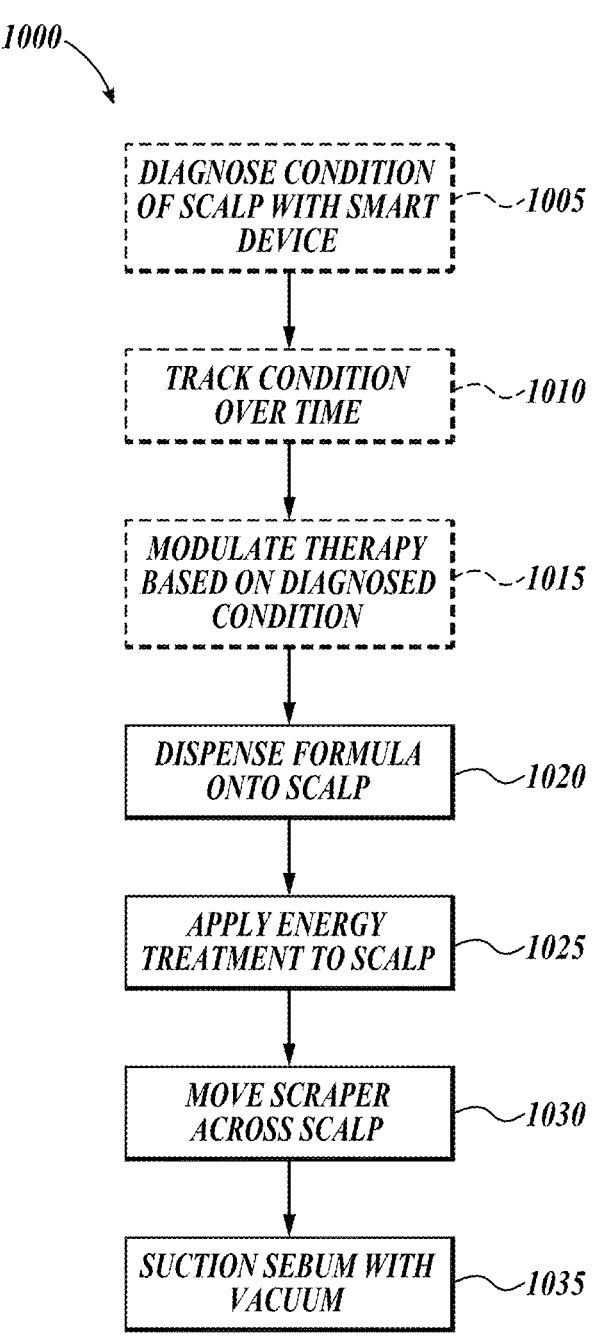
FIG. 10 is an example method for removing sebum, in accordance with the present technology.

FIG. 10 is an example method 1000 for removing sebum, in accordance with the present technology. In some embodiments, the method 1000 is carried out with the device (such as device 100) as described in detail herein. In some embodiments, the device includes a dispenser component (such as dispenser component 105), a transducer component (such as transducer component 115), a vacuum component (such as vacuum component 120), and a scraper component (such as scraper component 135) having one or more sebum extraction channels (such as one or more sebum extraction channels 140A, 140B . . . 140N). In some embodiments, the device includes a formula reservoir (such as formula reservoir 110), a suction tube (such as suction tube 125), a sebum reservoir (such as sebum reservoir 130), a processor (such as processor 145), a battery (such as battery 150), an actuator (such as actuator 155), and/or a guard (such as guard 160). In some embodiments, the device may be communicatively coupled to a smart device (such as smart device 900).

In block 1005, optionally, a condition of the scalp may be diagnosed with the smart device. In such embodiments, the smart device may include an application configured to take images (such as pictures or videos) of the scalp and use algorithms, such as segmentation algorithms, to determine the condition of the scalp. In some embodiments, the diagnosis may include excess sebum, dryness, redness, acne, dandruff, or the like.

In block 1010, optionally, the application may also track the condition over time. For example, the scalp may be imaged before therapy each time therapy is applied. In such embodiments, the smart device may determine an efficacy of the therapy.

In block 1015, optionally, the smart device may modulate therapy based on either the diagnosed condition and/or the tracked diagnosed condition. In some embodiments, modulating therapy includes identifying one or more areas of the scalp for therapy, modulating an ingredient of the formula, adjusting a temperature of the energy treatment, adjusting a frequency of the energy treatment, adjusting a wavelength of the energy treatment, or a combination thereof.

In block 1020, formula is dispensed onto the scalp. In some embodiments, the formula is applied to the scalp without touching the device to the scalp. In some embodiments, the formula is configured to clean the scalp without water.

In block 1025, energy treatment is applied to the scalp. In some embodiments, energy treatment includes heat treatment, ultrasonic vibration, and/or light treatment. In some embodiments, the energy treatment is configured to loosen sebum on the scalp.

In block 1030, the scraper component is moved across the scalp. In some embodiments, sebum is collected by the one or more sebum extraction channels on the scraper component. In some embodiments, the guard prevents the sebum from departing from the one or more sebum extraction channels.

In block 1035, suction is applied to the scalp and or the scraper component to remove and collect sebum from the scalp. In some embodiments, the sebum is suctioned into the suction tube and eventually into a sebum reservoir, which may be removed and cleaned between uses. In some embodiments, blocks 1025, 1030, and 1035 happen contemporaneously or simultaneously.

It should be understood that method 1000 should be interpreted as merely representative. In some embodiments, process blocks of method 1000 may be performed simultaneously, sequentially, in a different order, or even omitted, without departing from the scope of this disclosure.

The present application may reference quantities and numbers. Unless specifically stated, such quantities and numbers are not to be considered restrictive, but representative of the possible quantities or numbers associated with the present application. Also, in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

Embodiments disclosed herein may utilize circuitry in order to implement technologies and methodologies described herein, operatively connect two or more components, generate information, determine operation conditions, control an appliance, device, or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof.

An embodiment includes one or more data stores that, for example, store instructions or data. Non-limiting examples of one or more data stores include volatile memory (e.g., Random Access memory (RAM), Dynamic Random Access memory (DRAM), or the like), non-volatile memory (e.g., Read-Only memory (ROM), Electrically Erasable Programmable Read-Only memory (EEPROM), Compact Disc Read-Only memory (CD-ROM), or the like), persistent memory, or the like. Further non-limiting examples of one or more data stores include Erasable Programmable Read-Only memory (EPROM), flash memory, or the like. The one or more data stores can be connected to, for example, one or more computing devices by one or more instructions, data, or power buses.

In an embodiment, circuitry includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate that other embodiments within the scope of this disclosure may include structures and functionalities from more than one specific embodiment shown in the figures and described in the specification.

In the foregoing description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "vertical," "horizontal," "front," "rear," "left," "right," "top," and "bottom," etc. These references, and other similar references in the present application, are intended to assist in helping describe and understand the particular embodiment (such as when the embodiment is positioned for use) and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value. The term "based upon" means "based at least partially upon."

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

While illustrative embodiments have been illustrated and described, it will be appreciated that various changes can be made therein without departing from the spirit and scope of the invention.

We claim:

1. A device for reducing sebum, comprising:
a dispenser component configured to dispense a formula;
a transducer component configured to apply an energy treatment;
a vacuum component configured to apply suction; and
a scraper component comprising one or more sebum extraction channels, wherein the scraper component is configured to contact a scalp of a user, wherein the one or more sebum extraction channels comprise triangular, square, rectangular, or semi-circular grooves and wherein the one or more sebum extraction channels are a first one or more sebum extraction channels disposed on a contact surface of the scraper component, and a second one or more sebum extraction channels are disposed on a second side of the scraper component, opposite the contact surface.

2. The device of claim 1, further comprising:
a processor operably coupled to one or more of the dispenser component, the transducer component, the vacuum component, or the scraper component and configured to:
direct the dispenser component, transducer component, vacuum component, or scraper component; and
communicatively couple the device to a smart device.

3. The device of claim 1, wherein the one or more sebum extraction channels comprise groves having a geometric cross-section including regular or irregular shapes conical cross section shapes, or polygonal cross section shapes.

4. The device of claim 3, wherein the one or more sebum extraction channels are tapered.

5. The device of claim 1, wherein the energy treatment is ultrasonic vibration.

6. The device of claim 5, wherein a frequency of the ultrasonic vibration is between about 20 kHz to about 50 kHz.

7. The device of claim 1, wherein the energy treatment comprises light treatment.

8. The device of claim 7, wherein the light treatment is selected from red light having a wavelength of about 620 nm to about 750 nm, ultraviolet (UV) light having a wavelength of about 100 nm to about 400 nm, and infrared (IR) light having a wavelength of about 780 nm to about 1 mm.

9. The device of claim 1, wherein the energy treatment comprises heat treatment.

10. The device of claim 9, wherein the heat treatment heats the scalp to about 28 degrees Celsius to about 30 degrees Celsius.

11. The device of claim 1, wherein the device further comprises a guard; and a sebum reservoir, wherein the guard is configured for directing sebum to a sebum reservoir.

12. The device of claim 1, wherein the dispenser component comprises a nozzle, a pump, a sprayer, or a combination thereof.

13. The device of claim 1, wherein the device further comprises a formula reservoir configured to contain a formula.

14. The device of claim 13, wherein the formula reservoir is configured for piercing or opening a formula container.

* * * * *